(12) United States Patent
Lee et al.

US009739697B2

(10) Patent No.: US 9,739,697 B2
(45) Date of Patent: Aug. 22, 2017

(54) DROP IMPACT TESTER AND METHOD FOR DROP IMPACT TEST

(71) Applicant: Samsung Display Co., Ltd., Yongin, Gyeonggi-Do (KR)

(72) Inventors: Jong-Nam Lee, Hwaseong-si (KR); Ikjun Hong, Seoul (KR); Minsu Kim, Asan-si (KR)

(73) Assignee: Samsung Display Co., Ltd., Gyeonggi-do (KP)

( * ) Notice: Subject to any disclaimer, the term of this patent is extended or adjusted under 35 U.S.C. 154(b) by 243 days.

(21) Appl. No.: 14/657,197

(22) Filed: Mar. 13, 2015

(65) Prior Publication Data

US 2016/0047725 A1    Feb. 18, 2016

(30) Foreign Application Priority Data

Aug. 14, 2014  (KR) ........................ 10-2014-0106115

(51) Int. Cl.
*G01N 3/303*    (2006.01)

(52) U.S. Cl.
CPC .................................. *G01N 3/303* (2013.01)

(58) Field of Classification Search
USPC ........... 73/12.01, 12.04, 12.05, 12.06, 12.09, 73/12.11, 12.13
See application file for complete search history.

(56) References Cited

U.S. PATENT DOCUMENTS

| | | | |
|---|---|---|---|
| 6,374,661 B1 * | 4/2002 | Buratynski | G01N 3/30 73/12.06 |
| 9,057,660 B2 * | 6/2015 | Bin Jamaludin | G01M 7/08 |
| 2004/0200264 A1 * | 10/2004 | Chen | G01N 3/303 73/12.06 |
| 2005/0016256 A1 * | 1/2005 | Ishikawa | G01N 3/303 73/12.13 |
| 2006/0278026 A1 * | 12/2006 | Friedman | G01M 17/0078 73/865.6 |
| 2010/0162789 A1 * | 7/2010 | Su | G01N 3/303 73/12.06 |

(Continued)

FOREIGN PATENT DOCUMENTS

| | | |
|---|---|---|
| JP | 2005-030938 A | 2/2005 |
| JP | 3991255 B2 | 8/2007 |

(Continued)

*Primary Examiner* — Eric S McCall
(74) *Attorney, Agent, or Firm* — Knobbe Martens Olson & Bear LLP

(57) ABSTRACT

A drop impact tester comprises a holder configured to hold a test piece and release the test piece such that the test piece drops in freefall; an impact surface disposed under the holder such that the test piece dropped from the holder hits the impact surface; and a drop angle measurement device configured to measure a drop angle which is a value correlated with an angle between a major surface of the dropped test piece and a reference plane. The tester further comprises an impact measurement device configured to move the impact surface from its first posing state to its second posing state to adjust an angle of the impact surface with respect to the reference plane based on the drop angle. The impact measurement device is configured to measure a drop impact applied to the impact surface by the dropped test piece or another test piece.

20 Claims, 12 Drawing Sheets

(56) References Cited

U.S. PATENT DOCUMENTS

2013/0125616 A1* 5/2013 Bin Jamaludin ...... G01N 3/303
  73/12.01
2015/0292998 A1* 10/2015 Jeong .................... G01N 3/303
  73/12.13

FOREIGN PATENT DOCUMENTS

| JP | 4125317 B2 | 5/2008 |
|----|------------|--------|
| JP | 4311481 B2 | 5/2009 |
| KR | 10-0723494 B1 | 5/2007 |
| KR | 10-2007-0079355 A | 8/2007 |
| KR | 10-1118314 B1 | 3/2012 |

* cited by examiner

DROP IMPACT TESTER AND METHOD FOR DROP IMPACT TEST

CROSS-REFERENCE TO RELATED APPLICATIONS

This U.S. non-provisional patent application claims priority under 35 U.S.C. §119 of Korean Patent Application No. 10-2014-0106115, filed on Aug. 14, 2014, the entire contents of which are hereby incorporated by reference.

BACKGROUND

The present disclosure herein relates to a drop impact tester and a method for a drop impact test, and more particularly, to a drop impact tester and a method for a drop impact test capable of enhancing measuring accuracy.

Recently, with a trend toward downsizing, slimming and lightening, usage of portable electronic devices such as hand-held terminals, laptop computers, and the like have been steadily increasing.

For a hand-held terminal, a drop impact test is an essential prerequisite for considering an inoperative situation due to damage to an electronic device caused by a drop which may frequently happen by users during hand-held use.

In general, a drop impact tester is used for a drop impact test. A drop impact is affected by a drop height, a drop speed, a drop angle and the like. Particularly, an impulse and an impact angle of a test piece are different by the drop angle, and hence an apparatus and a method for a drop impact test capable of obtaining an accurate drop impact data according to a drop angle is required.

SUMMARY

The present disclosure provides a drop impact tester capable of measuring an accurate impact experienced by a test piece dropped.

Also, the present disclosure provides a method for a drop impact test capable of measuring an accurate impact experienced by a test piece dropped.

One aspect of the invention provides a drop impact tester comprising: a holder configured to hold a test piece comprising a major surface and a second surface facing away from the major surface such that the major surface of the test piece faces generally downward, the holder being further configured to release the test piece such that the test piece drops in freefall; an impact surface disposed under the holder such that the test piece dropped from the holder hits the impact surface; a drop angle measurement device configured to measure a drop angle which is a value correlated with an angle between the major surface of the dropped test piece and a reference plane; and an impact measurement device configured to move the impact surface from its first posing state to its second posing state to adjust an angle of the impact surface with respect to the reference plane based on the drop angle, the impact measurement device being further configured to measure a drop impact applied to the impact surface by the dropped test piece or another test piece.

In the foregoing tester, the impact measurement device may be configured to move the impact surface such that the angle of the impact surface with respect to the reference plane is substantially the same with the drop angle. The drop angle measurement device may comprise at least one among a camera, an ultraviolet sensor, an infrared sensor, and a laser sensor. The holder may comprise: an upper plate over which the test piece is disposed; and a rotating arm connected to the upper plate, and configured to rotate about a rotation axis to fix the test piece between the rotating arm and the upper plate or drop the test piece in freefall. The holder may further comprise: a second rotating arm spaced away from the rotating arm, and configured to rotate about a second rotation axis different from the rotation axis.

Still in the foregoing tester, the holder may comprise: an upper plate over which the test piece is disposed; and a grabber comprising at least one jaw disposed over the upper plate and the at least one jaw being movable with respect to the upper plate, the grabber being configured to move the at least one jaw for holding and releasing the test piece. The holder may further comprise a contact sensor configured to detect contact between the at least one jaw and the test piece. The test piece comprises a first side surface, a second side facing away from the first side surface, a third side surface connecting the first side surface and the second side surface, a fourth side surface connecting the first side surface and the second side surface and facing away from the third side surface, the first, second, third and fourth side surfaces defining a perimeter surface of the test piece, wherein the at least one movable jaw may comprise: a first jaw configured to move to contact the first side surface; a second jaw configured to move to contact the second side surface; a third jaw configured to move to contact the third side surface; and a fourth jaw configured to move to contact the fourth side surface. The test piece comprises a first side surface, a second side facing away from the first side surface, a third side surface connecting the first side surface and the second side surface, a fourth side surface connecting the first side surface and the second side surface and facing away from the third side surface, the first, second, third and fourth side surfaces defining a perimeter surface of the test piece, wherein the at least one jaw comprises: a fifth jaw configured to move to contact the first side and the third side surface; and a sixth jaw configured to move to contact the second side surface and the fourth side surface.

Further in the foregoing tester, the impact surface at its first posing state may define the reference plane, wherein the drop angle measurement device may be configured to measure an angle of the major surface of the dropped test piece with respect to the impact surface at its first posing state to acquire the drop angle, wherein the impact measurement device may be configured to move the impact surface to its second posing state in which an angle of the impact surface with respect to the major surface of the dropped test piece is substantially zero. The drop angle measurement device may be integrated with the impact measurement device. The drop impact tester may further comprise a controller configured to receive a signal indicative of the drop angle from the drop angle measurement device and provide a signal to change the angle of the impact surface with respect to the reference plane. The impact measurement device may be configured to move the impact surface to its second posing state such that substantially the entire portion of the major surface simultaneously hits the impact surface.

Another aspect of the invention provides a method of testing a drop impact of test pieces, the method comprising: holding a test piece comprising a major surface generally facing downward; releasing the test piece to drop in freefall toward an impact surface; measuring a drop angle which is a value correlated with an angle between the major surface of the dropped test piece and a reference plane; moving the impact surface from its first posing state to its second posing state to change an angle of the impact surface with respect to the reference plane based on the drop angle; and measuring a drop impact applied to the impact surface by the dropped test piece or another dropped test piece.

In the foregoing method, the impact surface may be moved such that the angle of the impact surface with respect to the reference plane is substantially the same with the drop angle. The measuring of the drop angle may be performed by at least one among a camera, an ultraviolet sensor, an infrared sensor and a laser sensor.

The impact surface at its first posing state may define the reference plane, wherein the measuring of the drop angle may comprise measuring an angle of the major surface of the dropped test piece with respect to the impact surface at its first posing state to acquire the drop angle, wherein the moving of the impact surface may comprise moving the impact surface to its second posing state in which an angle of the impact surface with respect to the major surface of the dropped piece is substantially zero. All of the measuring of the drop angle, the adjusting the angle of the impact surface and the measuring of the drop impact may be performed in a single freefall dropping of a test piece. The drop angle may be measured before the test piece reaches the impact surface or at a time when the test piece reaches the impact surface. The impact surface may be moved to its second posting state such that substantially the entire portion of the major surface simultaneously hits the impact surface.

A drop impact tester according to an exemplary embodiment of the present disclosure includes a dropping part, a drop angle measuring part, an impact measuring part and an impact surface angle changing part. The dropping part drops a test piece in freefall. The drop angle measuring part measures a drop angle of the test piece. The impact measuring part measures a drop impact of the test piece after the test piece is dropped and hits an impact surface thereof. The impact surface angle changing part changes an impact surface angle of the impact measuring part.

The impact surface angle changing part may change the impact surface angle to be equal to the drop angle.

The drop angle measuring part may include at least one among a camera, an ultraviolet sensor, an infrared sensor, and a laser sensor.

The dropping part may include an upper plate and a rotating fixture. The test piece may be disposed on the upper plate. The rotating fixture may be disposed on the upper plate, and rotate about a rotation axis to fix the test piece or drop the test piece in freefall.

The rotating fixture may include a first rotating fixture and a second rotating fixture. The first rotating fixture may rotate about a first rotation axis. The second rotating fixture may be spaced away from the first rotating fixture, and rotate about a second rotation axis different from the first rotation axis.

The dropping part may include an upper plate and a side fixture. The test piece may be disposed on the upper plate. The side fixture may be disposed on the upper plate and contact a side of the test piece to fix the test piece or to drop the test piece in freefall.

The dropping part may further include a contact sensor detecting a contact between the side of the test piece and the side fixture.

The side fixture may include a first side fixture, a second side fixture: a third side fixture and a fourth side fixture. The first side fixture may contact a first side of the test piece. The second side fixture may contact a second side spaced away from the first side. The third side fixture may contact a third side connected with the first side and the second side. The fourth side fixture may contact a fourth side which is connected with the first side and the second side and spaced away from the third side of the test piece.

The side fixture may include a fifth side fixture and a sixth side fixture. The fifth side fixture may contact the first side and the second side connected to the first side of the test piece. The sixth side fixture may contact the third side which is spaced away from the first side and connected to the second side, and the fourth side which is spaced away from the third side and connected to the second side.

The drop angle measuring part may measure an angle between the drop angle measuring part and the test piece dropped freely.

The drop angle measuring part may be included in the impact measuring part.

The drop impact tester according to an exemplary embodiment of the present disclosure may further include a control part which receives a drop angle signal corresponding to a drop angle from the drop angle measuring part and provides a start-of-changing-angle signal.

In other embodiments of the inventive concept, methods for a drop impact test include: fixing a test piece; dropping the fixed test piece in freefall; measuring a drop angle of the test piece dropped freely; changing an impact surface angle of an impact receiving surface of an impact measuring part on which the test piece is dropped and hits; and measuring a drop impact of the test piece.

The changing of an impact surface angle may be to change the impact surface angle to be equal to the drop angle.

The measuring of a drop angle may be performed by at least one among a camera, an ultraviolet sensor, an infrared sensor and a laser sensor.

The measuring of a drop angle may be to measure an angle between the drop angle measuring part and the test piece dropped freely.

When the dropping to freefall is performed once, the measuring of the drop angle and the changing of the impact surface angle and the measuring of the drop impact may be performed altogether.

DETAILED DESCRIPTION OF THE EMBODIMENTS

Objects, other objects, advantages and features of an embodiment of the inventive concept will be clarified through following embodiments described with reference to the accompanying drawings. The invention may, however, be embodied in many different forms and should not be construed as being limited to the embodiments set forth herein. Rather, these embodiments are provided so that this disclosure will be thorough and complete, and will fully convey the scope of an embodiment of the inventive concept to those skilled in the art.

In describing drawings herein, like reference symbols are used for like elements. Also, in the accompanying drawings, dimensions of structures may be exaggerated for clarity of illustration. The terms "first", "second" and the like may be used to describe various elements, but the elements should not be construed as limited by the terms. The terms are only used for the purpose of distinguishing one element from others. For example, without departing from the scope of claims of the present disclosure, "the first element" may be referred to as "the second elements", and vice versa. The terms of a singular form may include plural forms unless referred to the contrary.

In the present disclosure, the meaning of "include," "comprise," "including," or "comprising," specifies a property, a region, a fixed number, a step, a process, an element and/or a component but does not exclude other properties, regions, fixed numbers, steps, processes, elements and/or components. Furthermore, it will be understood that when a component is referred to as being 'on' another component, it can be directly on the other component, or an intervening component may also be present. On the contrary, it will be understood that when a component is referred to as being 'under' another component, it can be directly beneath the other component, or an intervening component may also be present.

Hereinafter, a drop impact tester according to an exemplary embodiment will be described in detail with reference to the accompanying drawings.

Figure 1:
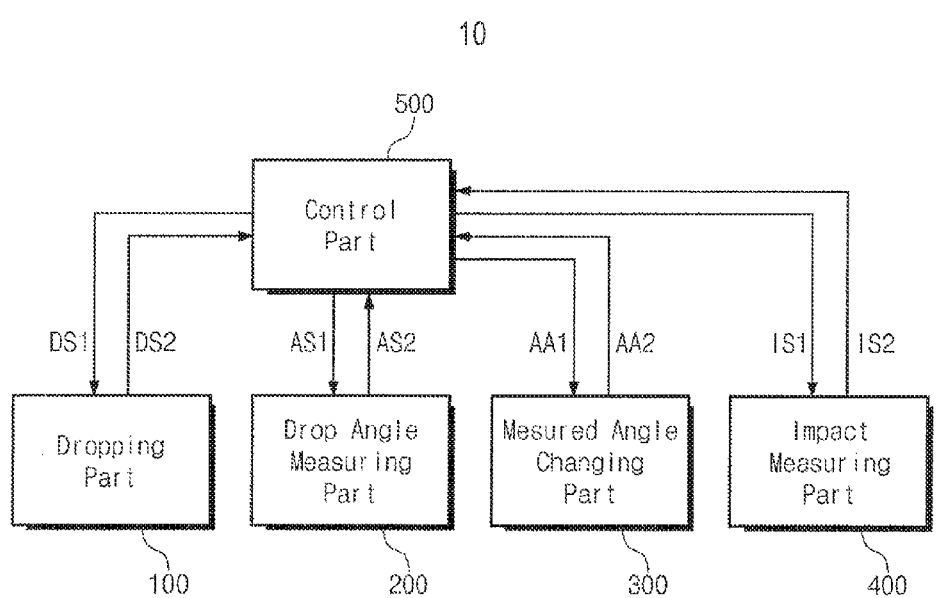
FIG. 1 is a block diagram schematically illustrating a drop impact tester according to an exemplary embodiment of the inventive concept.

FIG. 1 is a block diagram schematically illustrating a drop impact tester according to an exemplary embodiment of the inventive concept.

Referring to FIG. 1, a drop impact tester 10 according to an exemplary embodiment of the inventive concept includes a dropping part 100, a drop angle measuring part 200 and an impact surface angle changing part 300, an impact measuring part 400 and a control part 500.

The dropping part 100 drops a test piece or object 600 in freefall. When the test piece 600 is fixed to the dropping part 100, the dropping part 100 may receive a start-of-freefall signal from the control part 500 and drop the test piece 600 in freefall. When the freefall ends, the dropping part 100 may provide an end-of-freefall signal to the control part 500.

The test piece 600 may be a display device. The display device may be one of various display devices, for example, an organic light-emitting display device, a liquid crystal display device, a plasma display device, an electrophoresis display device and an electro-wetting display device. In embodiments, the test piece 600 may be a handheld device such as a smartphone, a tablet computer, and a laptop computer. In alternative embodiments, the test piece 600 may include any generally plate-shaped device or article or any generally bar-shaped article or device. In illustrated embodiments, the test object 600 may have a generally flat major surface. The generally flat major surface may be a display surface of a display apparatus. Alternatively, the generally flat major surface may be a surface of a display apparatus which faces away from its display surface.

In one embodiment, when drop-testing, the test object 600 may be held and released such that the major surface generally faces downward and that the major surface contacts the impact surface after dropped. In an alternative embodiment, when drop-testing, the test object 600 may be held and released such that the major surface generally faces upward, and that another surface of the test piece facing away from the major surface generally faces downward and contacts the impact surface after dropped.

Figure 2A:
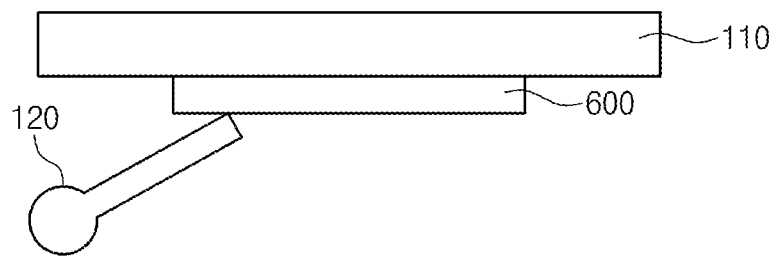
FIGS. 2A and 2B are side views schematically illustrating an operation process of a dropping part included in a drop impact tester according to an exemplary embodiment of the inventive concept.
Figure 2B:
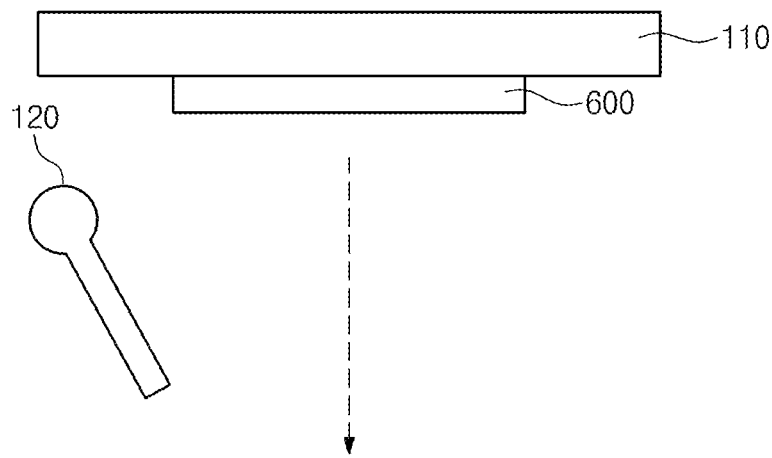

FIGS. 2A and 2B are side views schematically illustrating an operation process of a dropping part included in a drop impact tester 10 according to an exemplary embodiment of the inventive concept.

Referring to FIGS. 1, 2A and 2B, the dropping part 100 may include an upper plate 110 and a rotating fixture 120.

On the upper plate 110, the test piece 600 is disposed. The rotating fixture 120 is disposed on the upper plate 110 and rotates about an axis to contact the surface of the test piece 600 and fix the test piece 600. The rotating fixture 120 rotates about an axis to move apart from the test piece 600 and release the test piece 600 to drop in freefall.

FIGS. 2A and 2B exemplarily illustrates that the rotating fixture 120 is disposed away from the upper plate 110, but the rotating fixture 120 may be connected to the upper plate 110. When the rotating fixture 120 is disposed away from the upper plate 110, the rotating fixture 120 may be connected with one structure of the drop impact tester 10 according to an exemplary embodiment of the inventive concept to fix the position of the rotating fixture 120.

Although FIGS. 2A and 2B exemplarily illustrates that the rotating fixture 120 is disposed to the left of the upper plate 110, the inventive concept is not limited thereto, and thus the rotating fixture 120 may be disposed to the right of the upper plate 110.

Figure 3A:
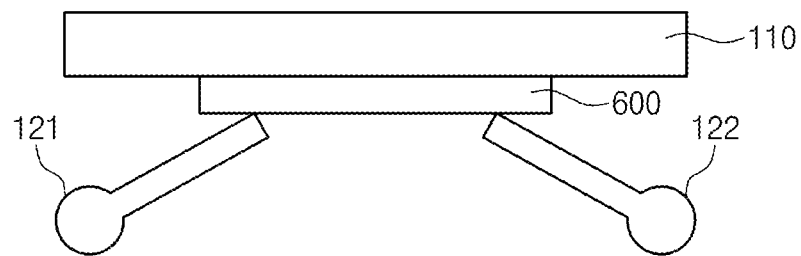
FIGS. 3A and 3B are side views schematically illustrating an operation process of a dropping part included in a drop impact tester according to an exemplary embodiment of the inventive concept.
Figure 3B:
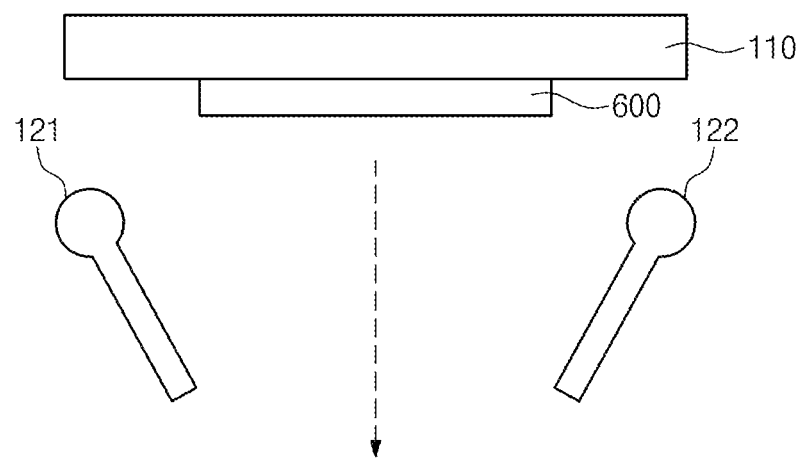

FIGS. 3A and 3B are side views schematically illustrating an operation process of the dropping part 100 included in the drop impact tester 10 according to an exemplary embodiment of the inventive concept.

Referring to FIGS. 1, 3A and 3B, the rotating fixture 120 may include a first rotating fixture 121 and a second rotating fixture 122.

The first rotating fixture 121 rotates about a first rotation axis. The second rotating fixture 122 is spaced away from the first rotating fixture 121 and rotates about a second rotation axis different from the first rotation axis.

Each of the first rotating fixture 121 and the second rotating fixture 122 contacts the upper surface of the test piece 600 to fix the test piece 600. Each of the first rotating fixture 121 and the second rotating fixture 122 may rotate about a rotation axis to move apart from the test piece 600 and releases the test piece 600 to drop in freefall.

FIGS. 3A and 3B exemplarily illustrate that the first rotating fixture 121 and the second rotating fixture 122 are disposed away from the upper plate 110, but the first rotating fixture 121 and the second rotating fixture 122 may be connected to the upper plate 110. When the first rotating fixture 121 and the second rotating fixture 122 are disposed away from the upper plate 110, the first rotating fixture 121 and the second rotating fixture 122 may be connected with one structure of the drop impact tester 10 according to an exemplary embodiment of the inventive concept to fix the positions of the first rotating fixture 121 and the second rotating fixture 122.

Figure 4A:
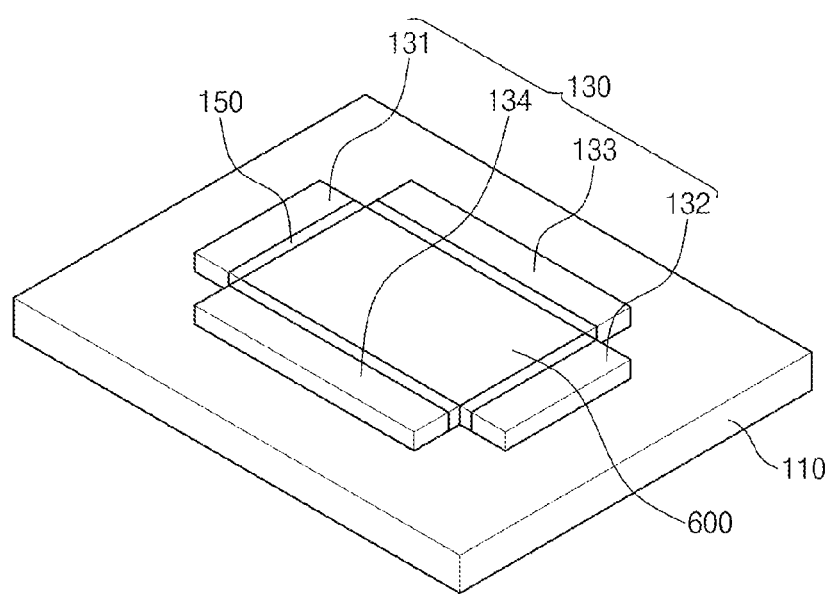
FIGS. 4A and 4B are perspective views schematically illustrating an operation process of a dropping part included in a drop impact tester according to an exemplary embodiment of the inventive concept.
Figure 4B:
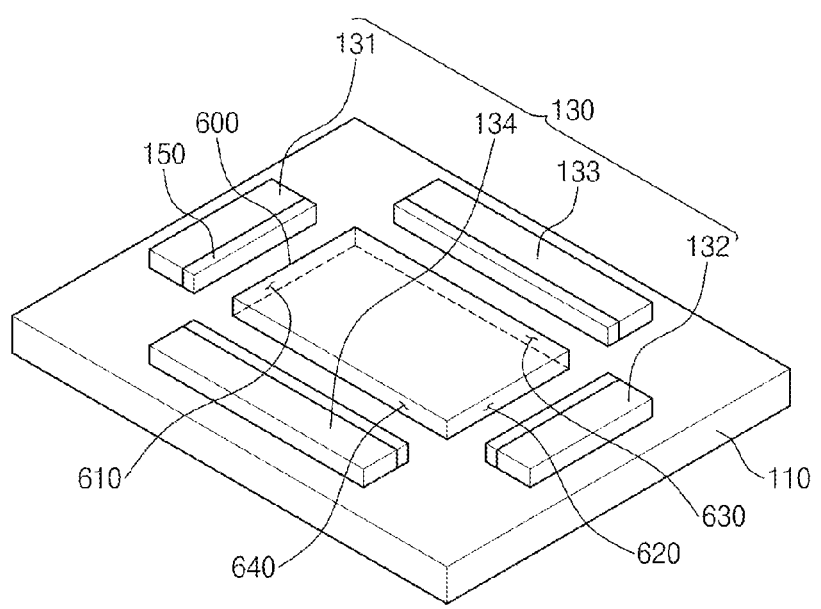

FIGS. 4A and 4B are perspective views schematically illustrating an operation process of the dropping part 100 included in the drop impact tester 10 according to an exemplary embodiment of the inventive concept.

Referring to FIGS. 1, 4A and 4B, the dropping part 100 may include an upper plate 110 and a side fixture 130. On the upper plate 110, the test piece 600 is disposed. The side fixture 130 is disposed on the upper plate 110 and contacts a side of the test piece 600 to fix the test piece 600 or drops the test piece 600 in freefall.

The side fixture 130 may include a first side fixture 131, a second side fixture 132, a third side fixture 133 and a fourth side fixture 134. The first side fixture 131 may contact a first side 610 of the test piece 600. The second side fixture 132 may contact a second side 620 spaced away from the first side 610. The third side fixture 133 may contact a third side 630 which is connected with the first side 610 and the second side 620. The fourth side fixture 134 may contact a fourth side 640 which is connected with the first side 610 and the second side 620 and spaced away from the third side 630.

Each of the first, second, third and fourth side fixtures 131, 132, 133 and 134 contacts sides of the test piece 600 to fix the test piece 600. Each of the first, second, third and fourth side fixtures 131, 132, 133 and 134 may move apart from the sides 610, 620, 630 and 640 of the test piece 600 and releases the test piece 600 to drop in freefall.

The dropping part 100 may further include a contact sensor 150 detecting a contact between the side of the test piece 600 and the side fixture 130. Upon detecting a contact between the side of the test piece 600 and the side fixture 130 by the contact sensor 150, the side fixture 130 may stop moving to prevent an external force from being unnecessarily applied during fixing of the test piece 600.

Although FIGS. 4A and 4B exemplarily illustrate that the contact sensor 150 is disposed to contact the side fixture 130, the inventive concept is not limited thereto, and thus the contact sensor 150 may be disposed to contact the rotating fixture (120 in FIGS. 2A and 2B) described above. The contact sensor 150 may be disposed to contact a fifth side fixture (see 135 in FIGS. 5A and 5B) and a sixth side fixture (136 in FIGS. 5A and 5B) which will be described below.

Figure 5A:
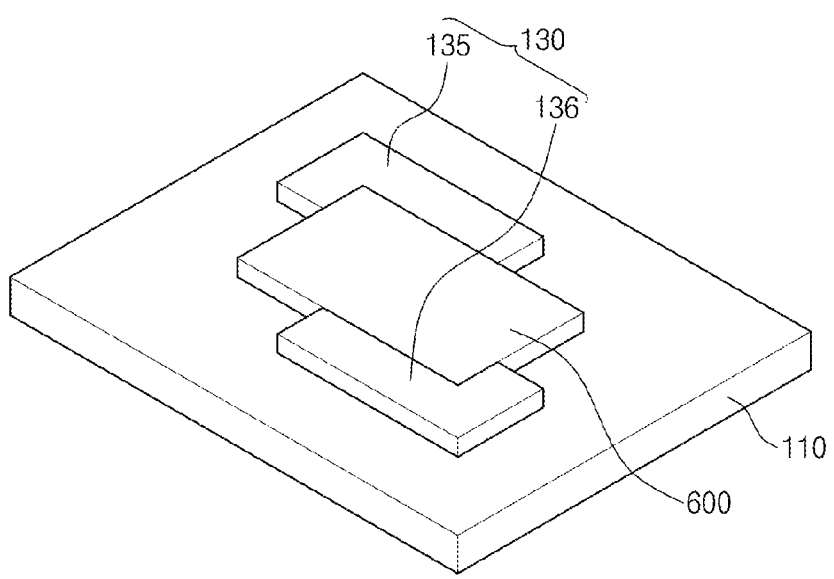
FIGS. 5A and 5B are perspective views schematically illustrating an operation process of a dropping part included in a drop impact tester according to an exemplary embodiment of the inventive concept.
Figure 5B:
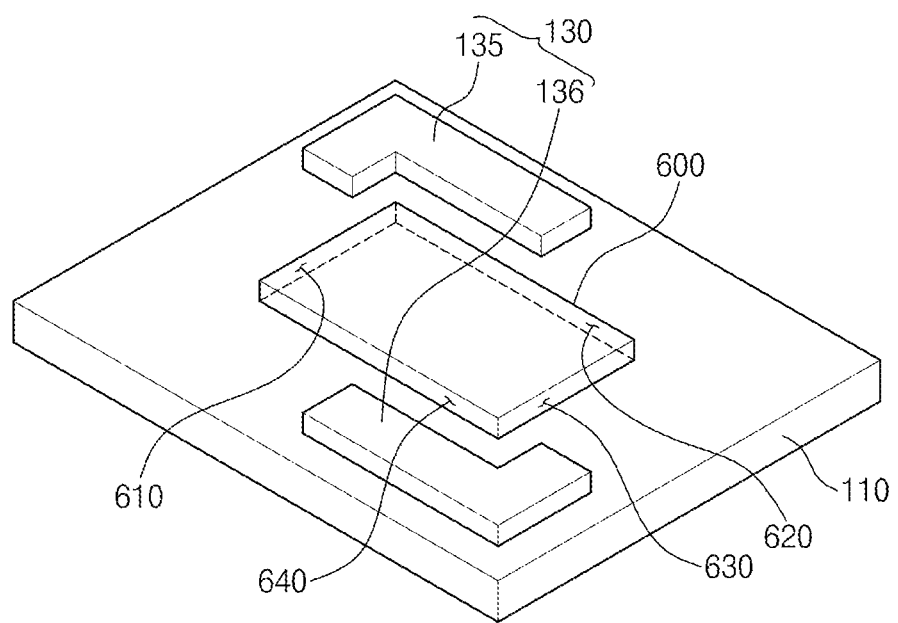

FIGS. 5A and 5B are perspective views schematically illustrating an operation process of the dropping part 100 included in the drop impact tester 10 according to an exemplary embodiment of the inventive concept.

Referring to FIGS. 1, 5A and 5B, the side fixture 130 may include a fifth side fixture 135 and a sixth side fixture 136.

The fifth side fixture 135 may contact the first side 610 and the second side 620 connected to the first side 610 of the test piece 600. The fifth side fixture 135 may contact at least a part of the first side 610 and at least a part of the second side 620.

The sixth side fixture 136 may contact the third side 630, which is spaced away from the first side 610 and connected to the second side 620, and the fourth side 640 which is spaced away from the second side 620 and connected to the third side 630. The sixth side fixture 136 may contact at least a part of the third side 630 and at least a part of the fourth side 640.

Each of the fifth side fixture 135 and the sixth side fixture 136 contacts the sides 610, 620, 630, 640 of the test piece 600 to fix the test piece 600. Each of the fifth side fixture 135 and sixth side fixture 136 moves away from the sides of the test piece 600 to drop the test piece 600 in freefall.

Figure 6A:
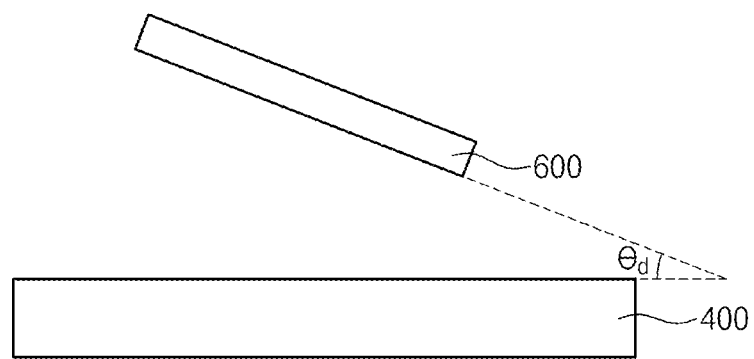
FIG. 6A is a view schematically illustrating a drop angle of a test piece in drop impact tester according to an exemplary embodiment of the inventive concept.

FIG. 6A is a view schematically illustrating a drop angle of the test piece 600 in the drop impact tester 10 according to an exemplary embodiment of the inventive concept.

Referring to FIGS. 1 and 6A, the drop angle measuring part 200 measures a drop angle $\Theta_d$ of the test piece 600. The drop angle measuring part 200 may, for example, measure an angle between an impact surface which, in embodiments, is an upper surface of the impact measuring part 400 and a major surface which, in embodiments, is a generally flat bottom surface of the test piece 600 dropped freely. In embodiments, the drop angle measuring part 200 may also measure an angle between the horizontal plane (HL in FIG. 6B) as a reference plane and the major surface of the test piece 600.

The drop angle measuring part 200 may receive a signal of start-of-measuring-drop-angle to measure the drop angle $\Theta_d$. The drop angle measuring part 200 may provide a signal of end-of-measuring-drop-angle to the control part 500 upon completing measuring of the drop angle $\Theta_d$. In embodiments illustrated in FIG. 6A, the drop angle $\Theta_d$ is illustrated to indicate an angle between the major surface of the test piece 600 and the horizontal plane, but the present invention is not limited thereto. In other embodiments, the measured drop angle may be a value that is different from but correlated with an angle between the major surface of the test piece 600 and the horizontal plane.

The drop angle measuring part 200 is not specifically limited as long as it is capable of measuring the drop angle $\Theta_d$, and may include, for example, at least one among a camera, an ultraviolet sensor, an infrared sensor and a laser sensor. The camera may be, for example, a charge coupled camera (CCD), a complementary metal oxide semiconductor (CMOS) camera and the like.

Figure 6B:
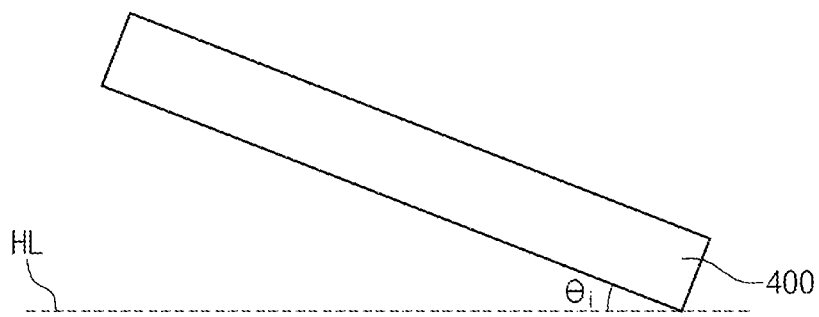
FIG. 6B is a view schematically illustrating an impact surface angle of the impact measuring part in a drop impact tester according to an exemplary embodiment of the inventive concept.

FIG. 6B is a view schematically illustrating an impact surface angle of an impact surface of the impact measuring part 400 in the drop impact tester 10 according to an exemplary embodiment of the inventive concept.

Figure 7:
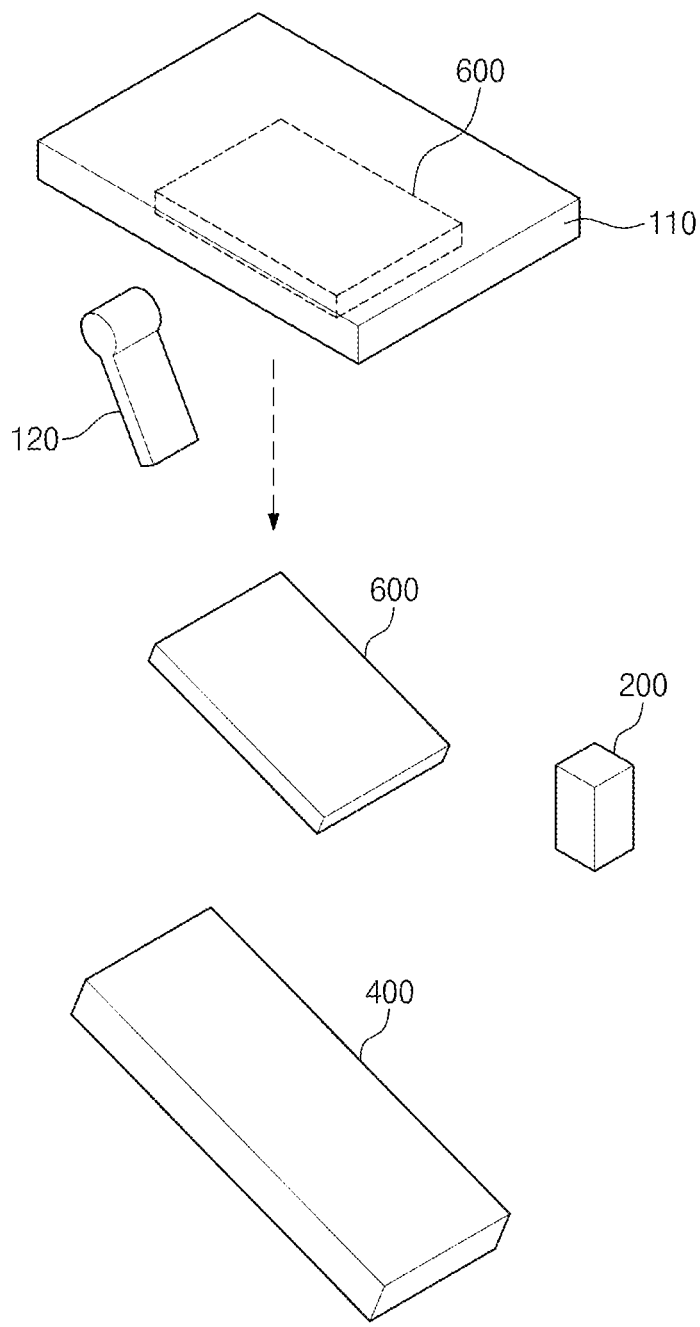
FIG. 7 is a perspective view schematically illustrating a drop impact tester according to an exemplary embodiment of the inventive concept.

FIG. 7 is a perspective view schematically illustrating the drop impact tester 10 according to an exemplary embodiment of the inventive concept. Although FIG. 7 exemplarily illustrates that the dropping part 100 includes the upper plate 110 and the rotating fixture 120, the inventive concept is not limited thereto, and thus the dropping part 100 may include the upper plate 110 and the side fixture 130.

Referring to FIGS. 1 and 6A, 6B and 7, the impact surface angle changing part 300 changes the impact surface angle $\Theta_i$ of the impact surface of the impact measuring part 400 as measured with respect from a reference plane. The impact surface angle $\Theta_i$ may be, for example, an angle made between the horizontal line HL and the impact surface of the impact measuring part 400 which is the upper surface in the illustrated embodiment. In embodiments, the impact surface may be moved from a first posing state of the impact measuring part 400 to a second posing state of the impact measuring part 400 having the impact surface angle $\Theta_i$. The impact surface angle changing part 300 may change or adjust the impact surface angle $\Theta_i$ to be substantially equal to the drop angle $\Theta_d$.

The impact surface angle changing part 300 may receive a start-of-changing-angle signal AA1 from the control part 500 to change the impact surface angle $\Theta_i$ of the impact measuring part 400. The impact surface angle changing part 300 may change the impact surface angle $\Theta_i$ of the impact measuring part 400 and, upon completing changing of the impact surface angle $\Theta_i$, may provide an end-of-changing-angle signal AA2.

The impact measuring part 400 measures a drop impact once the test piece 600 dropped freely hits the impact surface. The impact measuring part 400 measures an impulse of the test piece 600 and a collision angle made when the test piece 600 begins to contact the impact measuring part 400.

Figure 8:
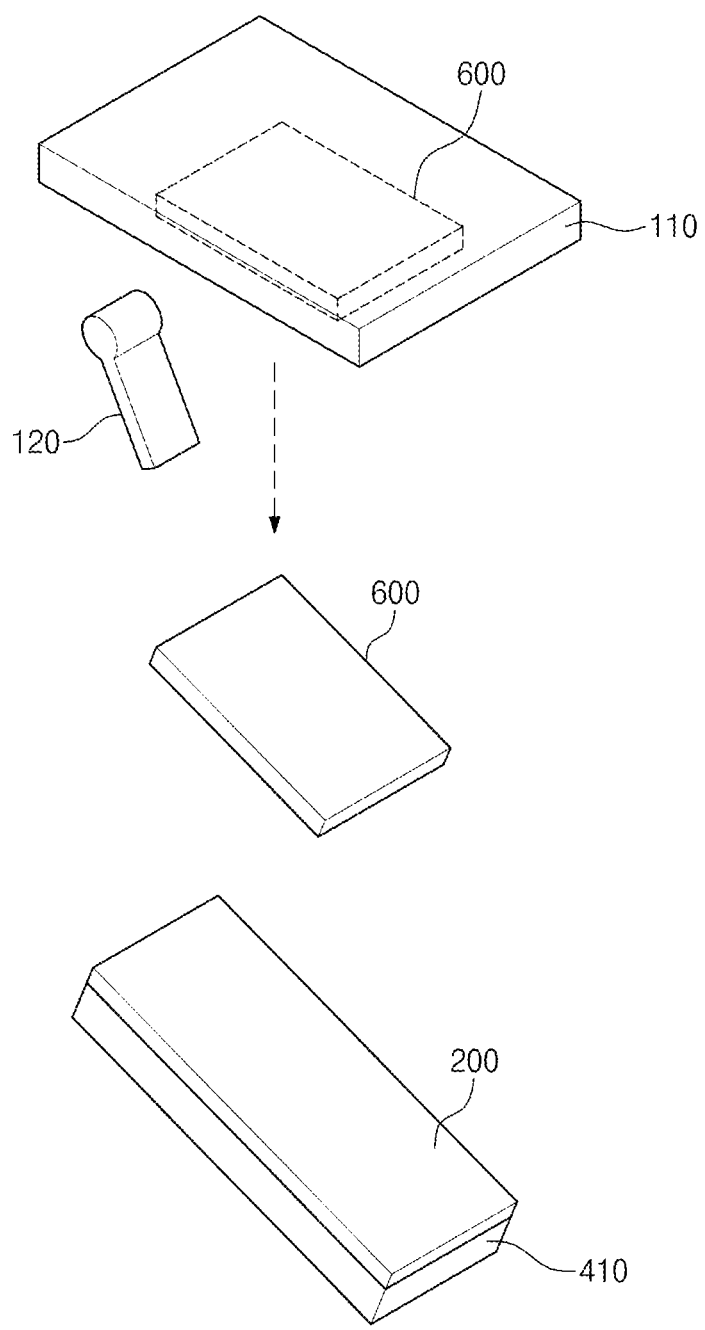
FIG. 8 is a perspective view schematically illustrating a drop impact tester according to an exemplary embodiment of the inventive concept.

FIG. 8 is a perspective view schematically illustrating the drop impact tester 10 according to an exemplary embodiment of the inventive concept. Although FIG. 8 exemplarily illustrates that the dropping part 100 includes the upper plate 110 and the rotating fixture 120, the inventive concept is not limited thereto, and thus the dropping part 100 may include the upper plate 110 and the side fixture (130 in FIG. 4A).

Referring to FIGS. 1 and 8, the impact measuring part 400 may include a lower plate 410. The lower plate 410 may be formed of a material capable of absorbing a shock of the test piece 600 dropped freely.

The impact measuring part 400 may include the drop angle measuring part 200. Since the impact measuring part 400 includes the drop angle measuring part 200, the impact measuring part 400 may measure the drop angle ($\Theta_d$ in FIG. 6A) before the test piece 600 dropped freely lay on the impact measuring part 400. For example, the drop angle measuring part 200 may be formed on the lower plate 410 and face the test piece 600 dropped freely. In the embodiment illustrated in FIG. 8, the drop angle measuring part 200 may be integrated with the impact measuring part 400 and may have an impact surface.

Referring to FIGS. 1, 7 and 8, the impact measuring part 400 may receive a start-of-measuring-impact signal IS1 from the control part 500 to measure an impulse and an impact angle of the test piece 600 dropped freely. After completing measuring the impulse and the impact angle, the impact measuring part 400 may supply an end-of-measuring-impact signal IS2 to the controller 500.

A drop impact is affected by a drop height, a drop speed and a drop angle and the like. Particularly, an impulse and an impact angle of a test piece are dependent on the drop angle, and thus a drop impact tester capable of obtaining an accurate drop impact data according to a drop angle is required.

The drop impact tester according to an exemplary embodiment of the inventive concept measures a drop angle of the test piece dropped freely and changes the impact surface angle of the impact measuring part. Thus, a deviation in the impact angle made when the test piece begins to contact the impact measuring part may be reduced, and thus a drop impact data may be measured accurately.

Hereinafter described will be a method for a drop impact test according to an exemplary embodiment of the inventive concept. Hereinafter, points that differ from the above-described drop impact tester according to the exemplary embodiment of the inventive concept, will be mainly described in detail, and elements that are not described will be appreciated as being the same as the above-described drop impact tester 10 according to the exemplary embodiment of the inventive concept.

Figure 9:
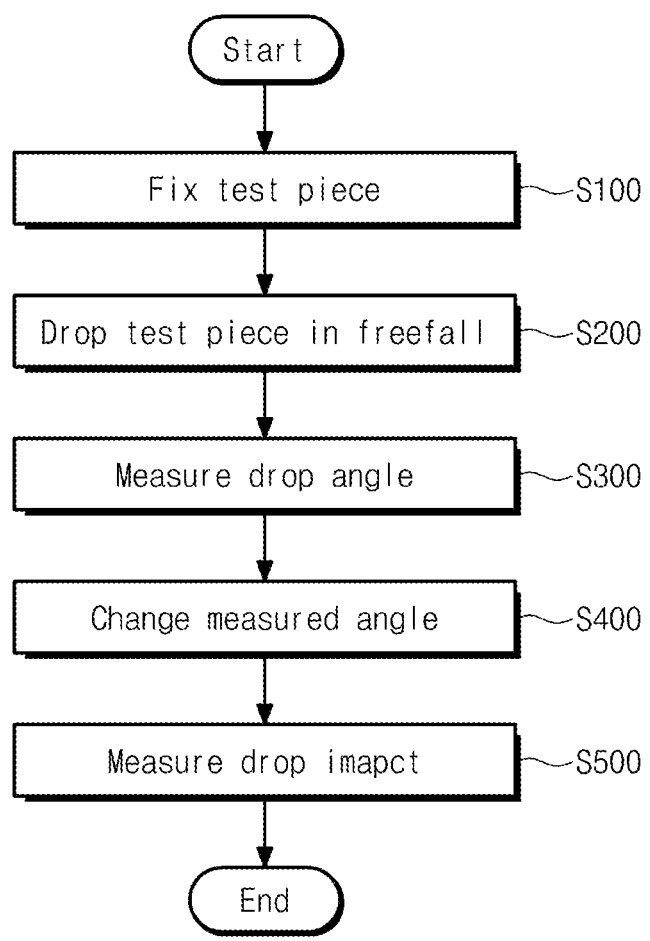
FIG. 9 is a flowchart schematically illustrating a method for a drop impact test according to an exemplary embodiment of the inventive concept.

FIG. 9 is a flowchart schematically illustrating a method for a drop impact test according to an exemplary embodiment of the inventive concept.

Referring to FIGS. 1, 7, 8 and 9, a method for a drop impact test according to an exemplary embodiment of the inventive concept may include: an operation (S100) of fixing a test piece 600; an operation (S200) of dropping the fixed test piece 600 in freefall; an operation (S300) of measuring a drop angle ($\Theta_d$ in FIG. 6A) of the test piece 600 dropped freely; an operation (S400) of changing an impact surface angle ($\Theta_i$ in FIG. 6B) of an impact measuring part 400 which the test piece 600 lay on; and an operation (S500) of measuring a drop impact of the test piece 600.

The operation (S100) of fixing the test piece 600 and the operation (S200) of dropping the fixed test piece 600 in freefall may be performed by a dropping part 100.

The dropping part 100 may include an upper plate 110 and a rotating fixture 120. On the upper plate 110, the test piece 600 is disposed. The rotating fixture 120 is disposed on the upper plate 110 and rotates about a rotation axis to contact an upper surface of the test piece 600 and fixes the test piece 600. Also, the rotating fixture 120 rotates about the rotation axis to move away from the test piece 600 and drops the test piece 600 in freefall.

Referring to FIGS. 1, 4A, 4B and 9, the dropping part 100 may include the upper plate 110 and a side fixture 130. On the upper plate 110, the test piece 600 is disposed. The side fixture 130 is disposed on the upper plate 110 and contact a side of the test piece 600 to fix the test piece 600 or allow the test piece 600 to fall freely.

Referring again to FIGS. 1, 4A, 4B and 9, a drop angle ($\Theta_d$ in FIG. 6A) of the test piece 600 dropped freely is measured in operation S300. The operation (S300) of measuring the drop angle ($\Theta_d$ in FIG. 6A) is performed by, any device not specifically limited as long as it is capable of measuring the drop angle $\Theta_d$, but, may be performed by at least one among a camera, an ultraviolet sensor, an infrared sensor and a laser sensor. The camera may be, for example, a charge coupled camera (CCD), a complementary metal oxide semiconductor (CMOS) camera and the like.

The operation (S300) of measuring the drop angle ($\Theta_d$ in FIG. 6A) may be performed to measure an angle between the impact measuring part 400 and the test piece 600 dropped freely.

An impact surface angle ($\Theta_i$ in FIG. 6B) of the impact measuring part 400 on which the test piece 600 is freely dropped is changed in operation S400. The operation (S400) of changing the impact surface angle ($\Theta_i$ in FIG. 6B) may be performed by the impact surface angle ($\Theta_i$ in FIG. 6B) changing part 300. The operation (S400) of changing the impact surface angle ($\Theta_i$ in FIG. 6B) may be performed to change the impact surface angle $\Theta_i$ to be equal to the drop angle $\Theta_d$.

A drop impact of the test piece 600 is measured in operation S500. The operation (S500) of measuring a drop impact may be performed by an impact measuring part 400. The impact measuring part 400 may measure a drop impact when the test piece 600 falls freely and lay thereon. The impact measuring part 400 may measure an impulse and impact angle of the test piece 600. The impact measuring part 400 may be formed of a material capable of absorbing a shock of the test piece 600 dropped freely.

In the method for a drop impact test according to an exemplary embodiment of the inventive concept, when the operation (S200) of dropping the test piece in freefall is performed once, the operation (S300) of measuring the drop angle ($\Theta_d$ in FIG. 6A), the operation (S400) of changing the impact surface angle ($\Theta_i$ in FIG. 6B), and the operation (S500) of measuring a drop impact may be performed altogether. But the inventive concept is not limited thereto. For example, when the operation (S200) of dropping the test piece in freefall is performed primarily, the operation (S300) of measuring the drop angle ($\Theta_d$ in FIG. 6A) and the operation (S400) of changing the impact surface angle ($\Theta_i$ in FIG. 6B) may be performed; however, the operation (S500) of measuring a drop impact may be performed when the operation (S200) of dropping the test piece in freefall is performed secondarily.

A drop impact is affected by a drop height, a drop speed and a drop angle and the like. Particularly, an impulse and an impact angle of a test piece are dependent on the drop angle, and thus a method for a drop impact test capable of obtaining an accurate drop impact data according to a drop angle is required.

The method for a drop impact test according to an exemplary embodiment of the inventive concept measures a drop angle of the test piece dropped freely and changes the impact surface angle of the impact measuring part. Accordingly, a deviation in the impact angle made when the test piece begins to contact the impact measuring part may be reduced, and thus a drop impact data may be measured accurately.

Hereinafter, inventive concept of the present disclosure will be described through more specific examples. The examples below are merely illustrative for ease of understanding of the inventive concept of the present disclosure and the scope of the inventive concept should not be construed as limited thereto.

EXAMPLES

Example 1

Prepared was a drop impact tester including a dropping part which includes an upper plate and a rotating fixture. A drop angle was measured using a charge coupled (CCD) camera as a drop angle measuring part, and the drop angle as measured here was about 1°. The impact surface angle of the impact measuring part was adjusted to be equal to the drop angle. After the impact surface angle was adjusted, a collision angle of the test piece (an angle made when the test piece begins to contact the impact measuring part) was measured 10 times.

Example 2

Prepared was the same drop impact tester as that of Example 1 except that a dropping part includes an upper plate, a first side fixture, a second side fixture, a third side fixture and a fourth side fixture. A drop angle was measured by a drop angle measuring part using a charge coupled (CCD) camera, and the drop angle as measured here was about 0°. The impact surface angle of the impact measuring part was adjusted to be identical to the drop angle. After the impact surface angle was adjusted, a collision angle of the test piece (an angle made when the test piece begins to contact the impact measuring part) was measured 10 times.

Comparative Example 1

Prepared was the same drop impact tester as that of Example 1 and a collision angle of the test piece was measured 10 times. The deviation in the collision angle (the difference between the maximum collision angle and the minimum collision angle) measured 10 times was about 3.42° in maximum.

Comparative Example 2

Prepared was the same drop impact tester as that of Example 2 and a collision angle of the test piece was measured 10 times. The deviation in the collision angle (the difference between the maximum collision angle and the minimum collision angle) measured 10 times was about 0.41° in maximum.

Experimental Results

Figure 10:
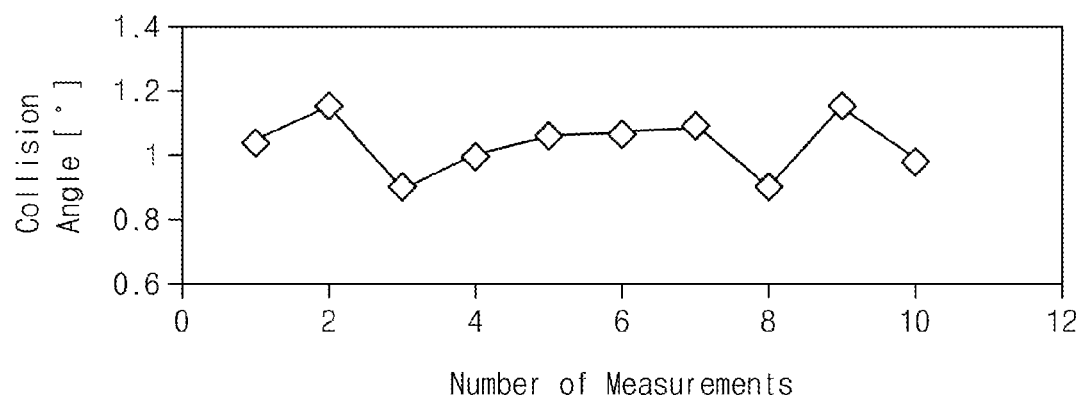
FIG. 10 is a graph showing the number of measurement and the collision angle according to Example 1 of the inventive concept.

The collision angle of the test piece measured in Example 1 is shown in FIG. 10. In Comparative example 1, the deviation in the collision angle (the difference between the maximum collision angle and the minimum collision angle) measured 10 times was about 3.42° in maximum; however, referring to FIG. 10, in Example 1, the deviation in the collision angle (the difference between the maximum collision angle and the minimum collision angle) measured 10 times was verified to be less than about 0.5°.

The deviation in the collision angle in Example 1 was less than that in Comparative example 1, and thus it was verified that a more accurate measurement of the collision angle might be possible in the former.

Figure 11:
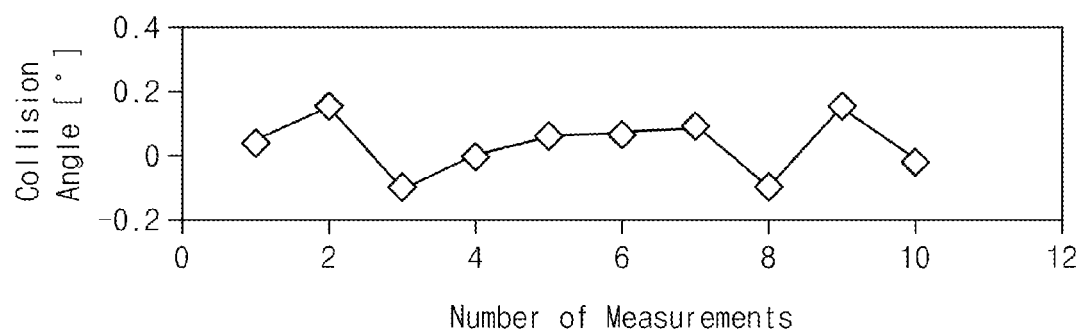
FIG. 11 is a graph showing the number of measurement and the collision angle according to Example 2 of the inventive concept.

The collision angle of the test piece measured in Example 2 is shown in FIG. 11. In Comparative example 2, the deviation in the collision angle (the difference between the maximum collision angle and the minimum collision angle) measured 10 times was about 0.41° in maximum; however, referring to FIG. 11, in Example 2, the deviation in the collision angle (the difference between the maximum collision angle and the minimum collision angle) measured 10 times was verified to be less than about 0.25°.

The deviation in the collision angle in Example 2 was less than that in Comparative example 2, and thus it was verified that a more accurate measurement of the collision angle might be possible in the former.

According to the drop impact tester according to an exemplary embodiment of the inventive concept, an impact experienced by a test piece dropped may be accurately measured.

Also, according to a method for a drop impact test according to an exemplary embodiment of the inventive concept, an impact experienced by a test piece dropped may be accurately measured.

The above-disclosed subject matter is to be considered illustrative and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:
1. A drop impact tester comprising:
   a holder configured to hold a test piece comprising a major surface and to release the test piece such that the test piece drops in freefall;
   an impact surface disposed under the holder such that the test piece dropped from the holder hits the impact surface;

a drop angle measurement device configured to measure a drop angle which is a value correlated with an angle between the major surface of the dropped test piece and a reference plane; and an impact measurement device configured to move the impact surface from its first posing state to its second posing state to adjust an angle of the impact surface with respect to the reference plane based on the drop angle, the impact measurement device being further configured to measure a drop impact impulse applied to the impact surface by the dropped test piece.

2. The drop impact tester of claim 1, wherein the impact measurement device is configured to move the impact surface such that the angle of the impact surface with respect to the reference plane is substantially the same with the drop angle.

3. The drop impact tester of claim 1, wherein the drop angle measurement device comprises at least one among a camera, an ultraviolet sensor, an infrared sensor, and a laser sensor.

4. The drop impact tester of claim 1, wherein the holder comprises:
an upper plate over which the test piece is disposed; and
a rotating arm connected to the upper plate, and configured to rotate about a rotation axis to fix the test piece between the rotating arm and the upper plate or drop the test piece in freefall.

5. The drop impact tester of claim 4, wherein the holder further comprises:
a second rotating arm spaced away from the rotating arm, and configured to rotate about a second rotation axis different from the rotation axis.

6. The drop impact tester of claim 1, wherein the holder comprises:
an upper plate over which the test piece is disposed; and
a grabber comprising at least one jaw disposed over the upper plate and the at least one jaw being movable with respect to the upper plate, the grabber being configured to move the at least one jaw for holding and releasing the test piece.

7. The drop impact tester of claim, 6, wherein the holder further comprises a contact sensor configured to detect contact between the at least one jaw and the test piece.

8. The drop impact tester of claim 6, wherein the test piece comprises a first side surface, a second side facing away from the first side surface, a third side surface connecting the first side surface and the second side surface, a fourth side surface connecting the first side surface and the second side surface and facing away from the third side surface, the first, second, third and fourth sides defining a perimeter surface of the test piece, wherein the at least one movable jaw comprises:
a first jaw configured to move to contact the first side surface;
a second jaw configured to move to contact the second side surface;
a third jaw configured to move to contact the third side surface; and
a fourth jaw configured to move to contact the fourth side surface.

9. The drop impact tester of claim 6, wherein the test piece comprises a first side surface, a second side facing away from the first side surface, a third side surface connecting the first side surface and the second side surface, a fourth side surface connecting the first side surface and the second side surface and facing away from the third side surface, the first, second, third and fourth sides defining a perimeter surface of the test piece, wherein the at least one jaw comprises:
a fifth jaw configured to move to contact the first side and the third side surface; and
a sixth jaw configured to move to contact the second side surface and the fourth side surface.

10. The drop impact tester of claim 1, wherein the impact surface at its first posing state defines the reference plane, wherein the drop angle measurement device is configured to measure an angle of the major surface of the dropped test piece with respect to the impact surface at its first posing state to acquire the drop angle, wherein the impact measurement device is configured to move the impact surface to its second posing state in which an angle of the impact surface with respect to the major surface of the dropped test piece is substantially zero.

11. The drop impact tester of claim 1, wherein the drop angle measurement device is integrated with the impact measurement device.

12. The drop impact tester of claim 1, further comprising a controller configured to receive a signal indicative of the drop angle from the drop angle measurement device and provide a signal to change the angle of the impact surface with respect to the reference plane.

13. The drop impact tester of claim 10, wherein the holder is configured to hold the test piece such that the major surface generally faces downward and contacts the impact surface after dropped, wherein the impact measurement device is configured to move the impact surface to its second posting state such that substantially the entire portion of the major surface simultaneously hits the impact surface.

14. A method of testing a drop impact of test pieces, the method comprising:
holding a test piece comprising a major surface;
releasing the test piece to drop in freefall toward an impact surface;
measuring a drop angle which is a value correlated with an angle between the major surface of the dropped test piece and a reference plane;
moving the impact surface to change an angle of the impact surface with respect to the reference plane based on the drop angle; and
measuring a drop impact impulse applied to the impact surface by the dropped test piece.

15. The method of claim 14, wherein the impact surface is moved to such that the angle of the impact surface with respect to the reference plane is substantially the same with the drop angle.

16. The method of claim 14, wherein the measuring of the drop angle is performed by at least one among a camera, an ultraviolet sensor, an infrared sensor and a laser sensor.

17. The method of claim 14, wherein the impact surface at its first posing state defines the reference plane, wherein the measuring of the drop angle comprises measuring an angle of the major surface of the dropped test piece with respect to the impact surface at its first posing state to acquire the drop angle, wherein the moving of the impact surface comprises moving the impact surface to its second posing state in which an angle of the impact surface with respect to the major surface of the dropped piece is substantially zero.

18. The method of claim 14, wherein all of the measuring of the drop angle, the adjusting the angle of the impact surface and the measuring of the drop impact impulse are performed in a single freefall drop of a test piece.

19. The method of claim. 14, wherein the drop angle is measured before the test piece reaches the impact surface or at a time when the test piece reaches the impact surface.

20. The method of claim 14, wherein the major surface generally faces downward and contacts the impact surface after dropped, wherein the impact surface is moved to its second posing state such that substantially the entire portion of the major surface simultaneously hits the impact surface.

\* \* \* \* \*